(12) United States Patent
Shiau (10) Patent No.: US 7,531,350 B2
(45) Date of Patent: May 12, 2009

(54) BIOREACTOR FOR GROWING FUNGUS, PLANT CELL, TISSUE, ORGAN, HAIRY ROOTS AND PLANTLET

(75) Inventor: Yih-Juh Shiau, Taichung (TW)

(73) Assignee: Agricultural Research Institute, Taichung (TW)

( * ) Notice: Subject to any disclaimer, the term of this patent is extended or adjusted under 35 U.S.C. 154(b) by 606 days.

(21) Appl. No.: 11/109,627

(22) Filed: Apr. 20, 2005

(65) Prior Publication Data

US 2006/0240544 A1    Oct. 26, 2006

(51) Int. Cl.
*C12M 1/00*    (2006.01)
(52) U.S. Cl. ............... 435/292.1; 435/295.2; 435/305.2; 435/299.1; 47/60
(58) Field of Classification Search ............... 435/292.1, 435/294.1, 291.3, 293.1, 305.2, 307.1, 299.1; 137/87.01; 211/1.52; 422/136, 155, 201, 422/253, 271, 291.8, 293.1; 210/619
See application file for complete search history.

(56) References Cited

U.S. PATENT DOCUMENTS

| | | | |
|---|---|---|---|
| 3,051,183 A * | 8/1962 | Jacobs ........................ 134/174 |
| 4,660,586 A * | 4/1987 | Knapp et al. ................... 137/2 |
| 4,857,464 A * | 8/1989 | Weathers et al. ............. 435/401 |
| 5,955,326 A * | 9/1999 | Bungay et al. ............... 435/101 |
| 6,680,200 B2 * | 1/2004 | Everett ........................ 435/420 |
| 6,753,178 B2 * | 6/2004 | Adelberg et al. ............. 435/261 |
| 2004/0096943 A1 * | 5/2004 | Marx et al. ................ 435/69.1 |
| 2004/0241835 A1 * | 12/2004 | Hutmacher et al. ...... 435/298.2 |

OTHER PUBLICATIONS

Chun-Zhao Liu, Yu-Chun Wang, Chen Guo, Fan Ouyang, He-Chun Ye, Guo-Feng Li, Production of artemisinin by shoot cultures of Artemisia annua L. in a modified inner-loop mist bioreactor. Plant Scinces. 1998, vol. 135, pp. 211-217. Elsevier Science Ireland, Ltd.*
Yoojeong Kim et. al.; *invited Review: Secondary Metabolism Of Hairy Root Cultures In Bioreactors*; 2002; Society for In Vitro Biology; In Vitro Cell Dev. Biol.—Plant, vol. 38, pp. 1-10.
Jeffrey L. Fox; *Plants Thrive In Ultrasonic Nutrient Mists*; Apr. 1988; Bio/Technology, vol. 6; pp. 361.
Argyrios Margaritis et. al.; *Novel Bioreactor Systems And Their Applications*; May 1984; Bio/Technology; pp. 447-453.
Shinsaku Takayama et. al.; *The types of bioreactors used for shoots and embryos*; 1994; Plant Cell, Tissue and Organ Culture 39; pp. 147-156.

* cited by examiner

*Primary Examiner*—William H Beisner
*Assistant Examiner*—Michael Hobbs
(74) *Attorney, Agent, or Firm*—Bacon & Thomas, PLLC (57) ABSTRACT

A bioreactor includes a nutrient reservoir, a rotatable culture bed, at least one culture carrier medium, a mist generator and a mist delivery pipe. The nutrient reservoir stores therein a nutrient solution required for the fungus, plant cell, tissue, organ, hairy roots and plantlet. The rotatable culture bed is rotated at a specified speed. The at least one culture medium has thereon the fungus, plant cell, tissue, organ, hairy roots and plantlet and is supported on the rotatable culture bed. The mist generator is used for producing mists of the nutrient solution. The mist delivery pipe delivers therein the mists of the nutrient solution and has a mist-exit port adjusted to a desired level above the culture medium so as to discharge and spray the mists over the fungus, plant cell, tissue, organ, hairy roots and plantlet.

19 Claims, 6 Drawing Sheets

Fig. 1

PRIOR ART

BIOREACTOR FOR GROWING FUNGUS, PLANT CELL, TISSUE, ORGAN, HAIRY ROOTS AND PLANTLET

FIELD OF THE INVENTION

The present invention relates to a bioreactor, and more particularly to a mist bioreactor for growing fungus, plant cell, tissue, organ, hairy roots and plantlet.

BACKGROUND OF THE INVENTION

Figure 1:
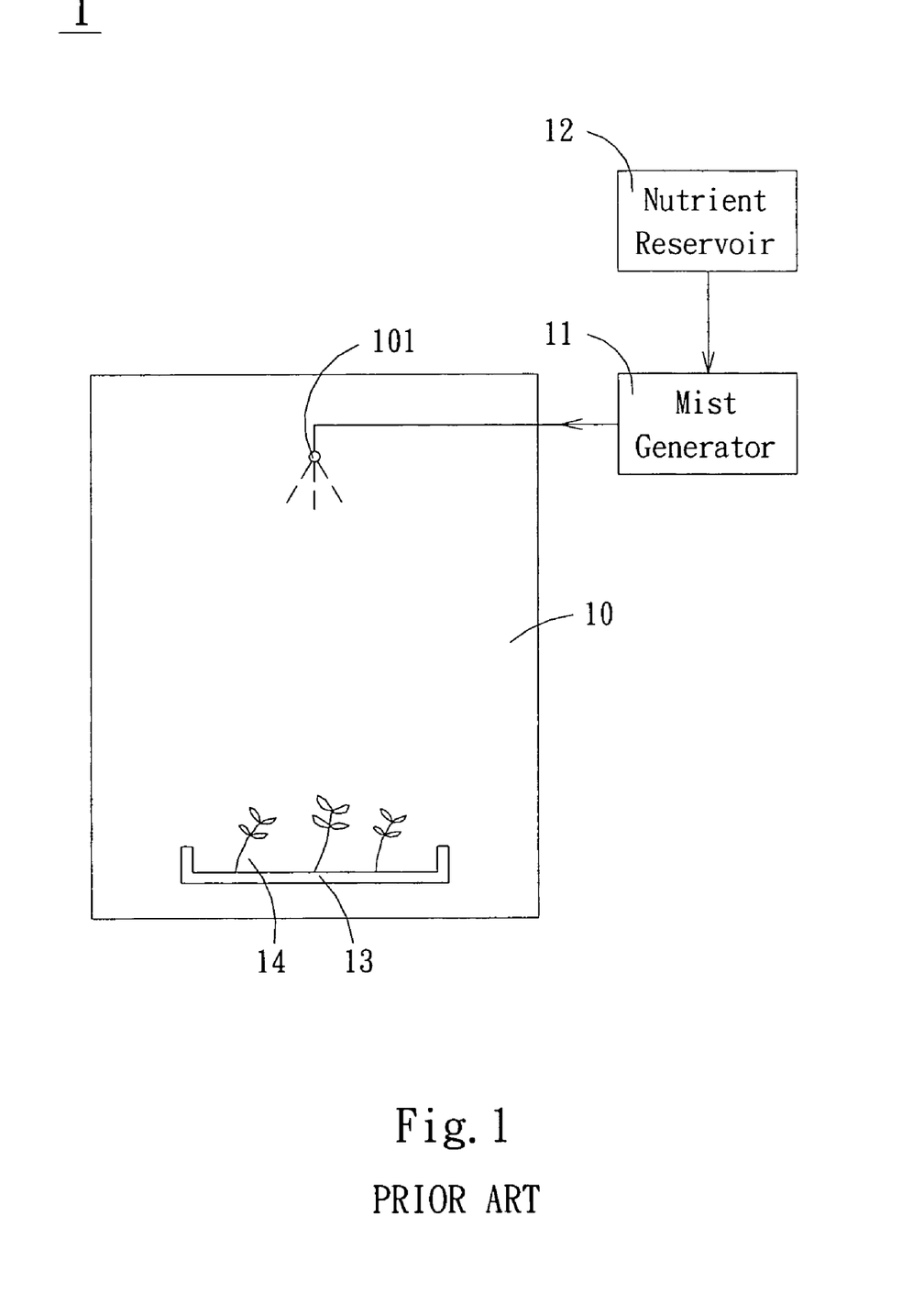
FIG. 1 schematically illustrates a conventional mist bioreactor.

With increasing development of bioengineering technologies, many valuable funguses, plants or their secondary metabolites are propagated and produced in bioreactors. Most of bioreactors were used for propagating fungus hypha or plant cell. These bioreactors comprise stirred tanks, bubble columns, air-lift reactors, hollow-fiber membranes, liquid-dispersed trickle and incline reactors. Some of bioreactors were capable used to culture plantlet, for example mist bioreactors. As known, each of these bioreactors has several limitations. Take a conventional mist bioreactor for example. Referring to FIG. 1, the mist bioreactor 1 comprises a growth chamber 10, an ultrasonic mist generator 11 and a nutrient reservoir 12. In the growth chamber 10, a culture medium 13 has thereon explants 14 to be propagated, for example three plantlets. The nutrient solution of the nutrient reservoir 12 flows into the ultrasonic mist generator 11 and is energized by the ultrasonic mist generator 11, thereby creating nutrient mists. The nutrient mists are then discharged from a mist-exit port 101 and distributed over the plantlets 14. The locations of the mist-exit port 101 and the culture medium 13 are unchanged. As known, the mist-exit port 101 spreads more nutrient mists onto the middle shoot, while the bilateral shoots get less nutrient mists. Therefore, the plantlet 14 has different growth rate. In addition, the industrial application of such a bioreactor has been limited by a number of drawbacks including low product yields and difficulty in scale-up.

SUMMARY OF THE INVENTION

It is therefore an object of the present invention to provide a bioreactor capable of growing fungus, plant cell, tissue, organ, hairy roots and plantlet at substantial growth rate and increased product yields.

It is another object of the present invention to provide a bioreactor, in which the nutrient mists are uniformly distributed on the explants in a short time period.

It is still an object of the present invention to provide a portable bioreactor, which is light and simple in structure.

In accordance with a first aspect of the present invention, there is provided a bioreactor for growing fungus, plant cell, tissue, organ, hairy roots and plantlet. The bioreactor comprises a nutrient reservoir, a rotatable culture bed, at least one culture medium, a mist generator and a mist delivery pipe. The nutrient reservoir stores therein a nutrient solution required for the explants. The rotatable culture bed is rotated at a specified speed. The at least one culture medium has thereon the explants and is supported on the rotatable culture bed. The mist generator is used for producing mists of the nutrient solution. The mist delivery pipe delivers therein the mists of the nutrient solution and has a mist-exit port adjusted to a desired level above the culture medium so as to discharge and spray the mists over the explants.

In an embodiment, the bioreactor further comprises a constant-level tank disposed between the nutrient reservoir and the mist generator for ensuring that the nutrient solution flowing into the mist generator at a constant rate.

In an embodiment, the mist generator is an ultrasonic mist generator, and comprises a nutrient inlet for introducing the nutrient solution therethrough, an ultrasonic transducer for creating microwaves to energize the nutrient solution to create the mists, and a gas inlet for introducing a proper amount of gas sources necessary for cultivating the explants therethrough.

In an embodiment, the bioreactor further comprises a gas pump in upstream of the gas inlet for increasing the velocity of the gas sources flowing through the nutrient inlet.

In an embodiment, the bioreactor further comprises a servo motor for driving rotation of the rotatable culture bed.

In an embodiment, the mist delivery pipe has a lower end in communication with the mist generator and a closed upper end.

In an embodiment, the mist delivery pipe is arranged in an upright position.

In an embodiment, the mist delivery pipe comprises a fixed inner tube and a rotatable outer tube. The inner tube delivers therein the mists of the nutrient solution, and comprises first and second openings arranged on a side facing the rotatable culture bed. The outer tube surrounds the inner tube, and comprises third and fourth openings corresponding to the first and second openings and arranged on opposite sides of the outer tube, respectively. When the outer tube is rotated such that the third opening is aligned with the first opening, the third opening serves as the mist-exit port. Whereas, when the outer tube is rotated such that the fourth opening is aligned with the second opening, the fourth opening serves as the mist-exit port.

In an embodiment, the bioreactor further comprises a light source required for metabolism of the fungus, plant cell, tissue, organ, hairy roots and plantlet.

In an embodiment, the light source is a LED lamp.

In an embodiment, the rotatable culture bed, the culture medium and the mist delivery pipe are disposed within a growth chamber.

In an embodiment, the growth chamber further comprises a drain port at the bottom thereof for draining excess nutrient solution.

In an embodiment, the growth chamber further comprises at least a vent at the top thereof.

In an embodiment, the growth chamber further comprises at least a side door selectively opened for placing the culture medium thereinto or removing the culture medium therefrom.

In an embodiment, the at least one culture medium comprises more than two culture media.

In an embodiment, the rotatable culture bed comprises a lower end ring, a top end ring and at least one intermediate ring, and the culture media are supported on the lower end ring and the intermediate ring of the rotatable culture bed.

In an embodiment, the lower end ring, the top end ring and the at least one intermediate ring are jointed together by more than two upright posts.

In an embodiment, the top and lower end rings have several first ribs extended to center portions thereof.

In an embodiment, the intermediate ring has several protrusion structures for supporting the culture medium.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 2:
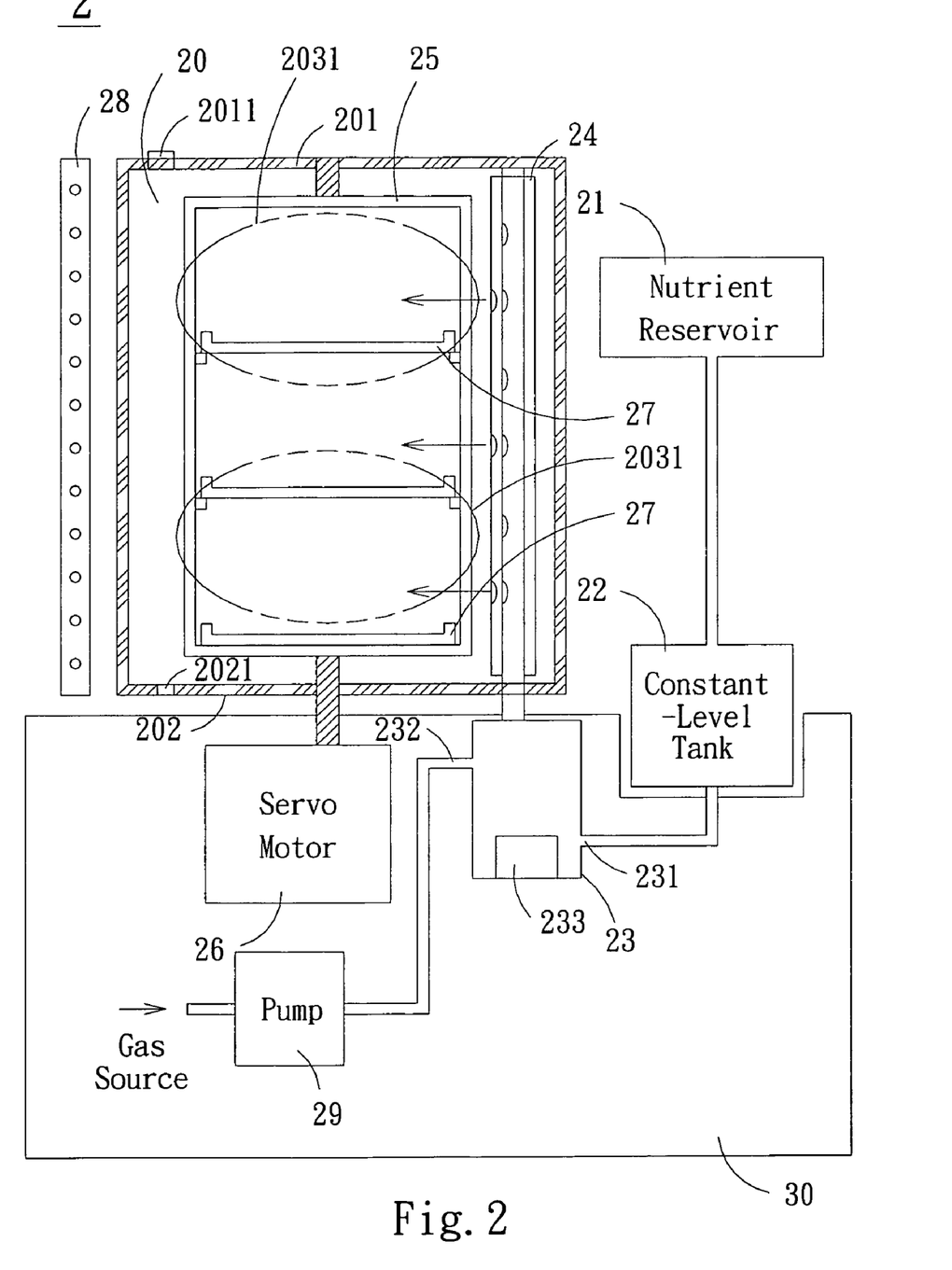
FIG. 2 schematically illustrates a mist bioreactor according to a preferred embodiment of the present invention.

Referring to FIG. 2, a schematic view of a mist bioreactor according to a preferred embodiment of the present invention is shown. The bioreactor 2 principally comprises a nutrient reservoir 21, a constant-level tank 22, an ultrasonic mist generator 23, a mist delivery pipe 24, a rotatable culture bed 25, a servo motor 26, at least one culture medium 27 and optionally a light source 28. The servo motor 26 is disposed within a box 30. The mist delivery pipe 24 and the rotatable culture bed 25 are disposed within a growth chamber 20, which sealable to maintain non-pollutant conditions and can be supported on the box 30. The growth chamber 20 is advantageously made of transparent materials such as polycarbonate. In an embodiment, the growth chamber 20 is fabricated from six polycarbonate sheets to form a rectangular solid main body.

The explants to be propagated in the bioreactor of the present invention include fungus, plant cell, tissue, organ, hairy roots or the plantlets themselves. For example, stems or shoots can be used to propagate potatoes, alfalfa, carrots and the like. The hairy roots of yew trees (*Taxus* Linn.) or ginkgo trees can be used to propagate yew trees or ginkgo trees and produce pacilitaxel. In addition, some curative fungus such as *Antrodia camphorate* are also suitable for propagation in the bioreactor of the present invention.

The nutrient reservoir 21 contains the nutrient solution required for the explants to be grown, for example carbohydrate and nitrogen sources, salts, water and optionally hormones.

The constant-level tank 22 is disposed between the nutrient reservoir 22 and the ultrasonic mist generator 23 for ensuring that the nutrient solution flowing into the ultrasonic mist generator 23 at a constant rate. The operation principle of the constant-level tank 22 is known to those skilled in the art, and needs not be described redundantly herein.

The ultrasonic mist generator 23 is disposed under the growth chamber 20, and comprises a nutrient inlet 231, a gas inlet 232 and an ultrasonic transducer 233. Via the nutrient inlet 231, the nutrient solution stored in the nutrient reservoir 21 is introduced into the ultrasonic mist generator 23. The nutrient solution is then energized by the microwaves created from the ultrasonic transducer 233, thereby creating nutrient mists. In addition, a proper amount of gas sources necessary for cultivating the explants, for example air, oxygen-rich air or carbon dioxide in the aerobic condition or nitrogen in the anaerobic condition, may be introduced into the growth chamber 20 via the gas inlet 232. Furthermore, for increasing the velocity of the gas sources flowing through the nutrient inlet 232, a gas pump 29 is provided in upstream of the gas inlet 232. By the way, the pumped gas source can facilitate dispersing the nutrient mists.

Figure 3:
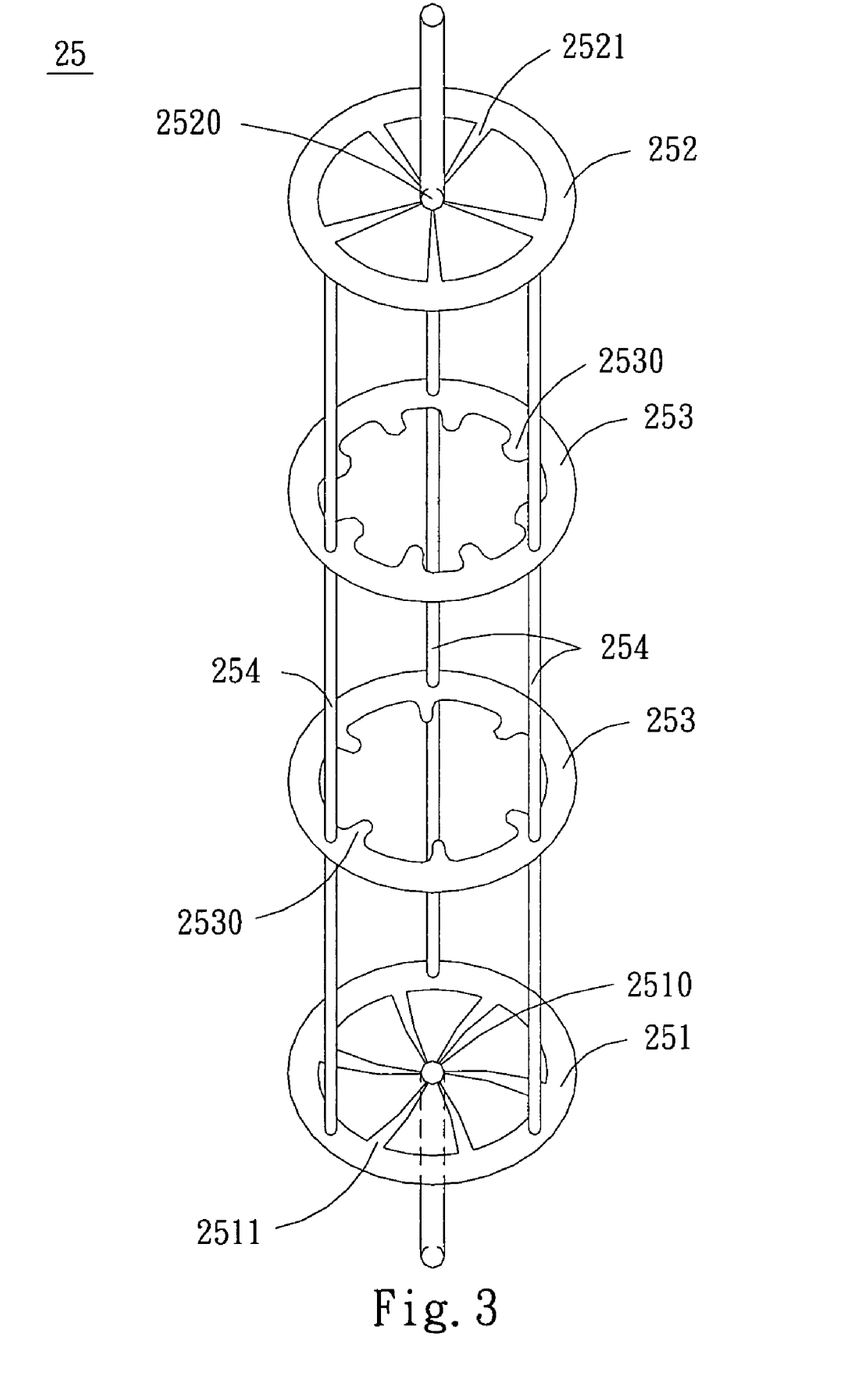
FIG. 3 schematically illustrates a perspective view of a rotatable culture bed used in the mist bioreactor of FIG. 2.

Please refer to FIGS. 2 and 3. The rotatable culture bed 25 comprises a lower end ring 251, a top end ring 252 and two intermediate rings 253. The lower end ring 251, the top end ring 252 and the intermediate rings 253 are jointed together by more than two upright posts 254. The top end ring 252 has several ribs 2521 extended to the center portion 2520, and the center portion 2520 is pivotally coupled to the top cover 201 of the growth chamber 20. The lower end ring 251 has several ribs 2511 extended to the center portion 2510, and the center portion 2510 is pivotally coupled to the servo motor 26. Each of the intermediate rings 253 has several protrusion structures 2530 for supporting the culture medium 27. Since each of the lower end ring 251 and the intermediate rings 253 can support one culture medium 27, the rotatable culture bed 25 of this embodiment can support at most three culture media 27. The culture medium 27 is made of biologically inert material. The explants to be grown should be placed on the culture medium 27, and then the culture medium 27 with the explants are supported on one of the lower end ring 251 and the intermediate rings 253. When the rotatable culture bed 25 is driven by the servo motor 26, the rotatable culture bed 25 can be rotated at a specified speed and thus the culture media 27 supported thereon are also rotated. Upon rotation of the culture media 27, the nutrient mists are distributed on the explants more uniformly.

Figure 4A:
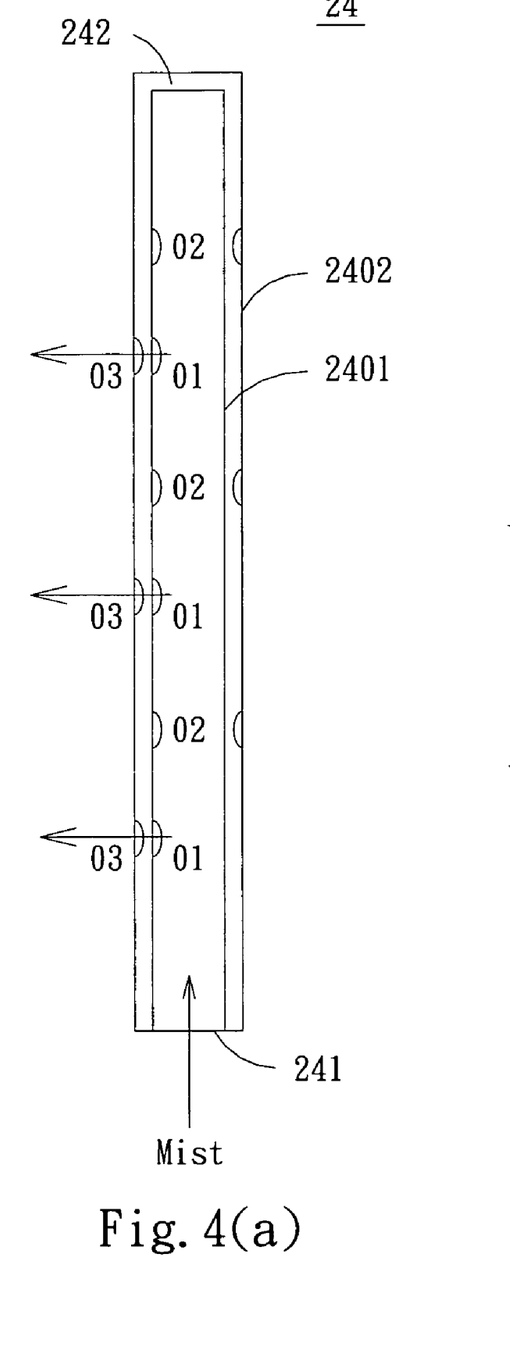
FIGS. 4(a) and 4(b) schematically illustrates a mist delivery pipe having adjustable mist-exit ports.
Figure 4B:
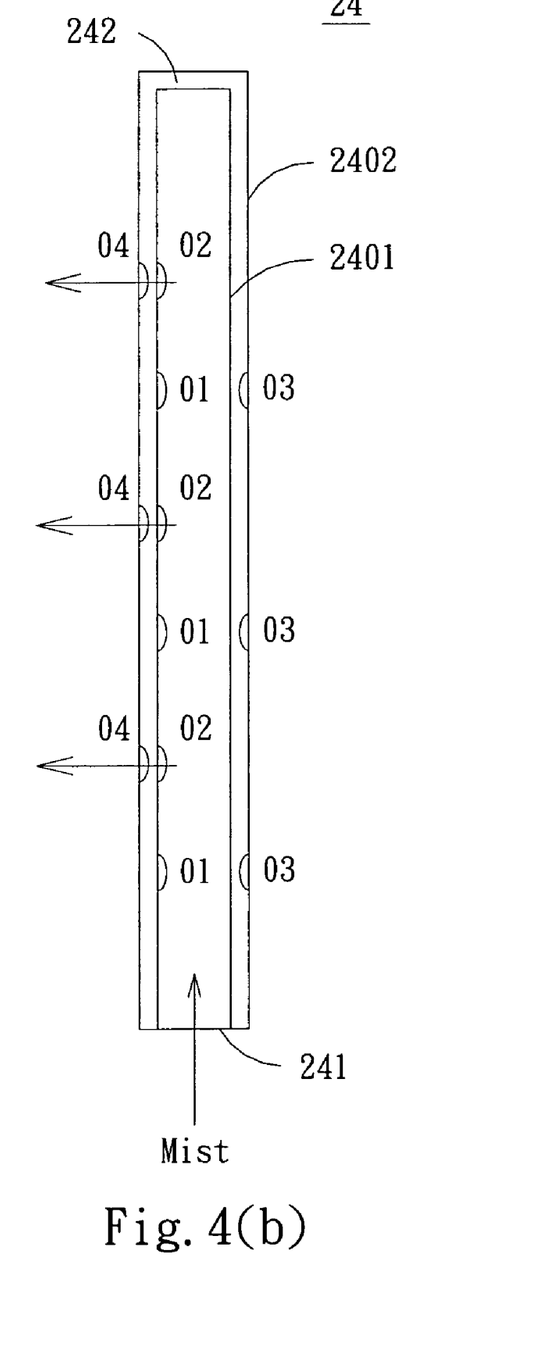

Please refer to FIGS. 2 and 4. The mist delivery pipe 24 is arranged in an upright position and supported by the bottom cover 202 of the growth chamber 20. The lower end 241 of the mist delivery pipe 24 is in communication with the ultrasonic mist generator 23. Whereas, the upper end 242 of the mist delivery pipe 24 can be closed and slightly protruded from the top cover 201 of the growth chamber 20. The mist delivery pipe 24 is employed to deliver nutrient mists from the ultrasonic mist generator 23. The mist delivery pipe 24 is composed of a fixed inner tube 2401 and a rotatable outer tube 2402. For each culture medium 27, the fixed inner tube 2401 comprises at least a first opening O1 and a second opening O2, which are arranged on the side facing the rotatable culture bed 25. The upper end 242 of the outer tube 2402 can be manually rotated so as to adjust the mist-exit port to a desired level above the culture medias 27. The outer tube 2402 has a third opening O3 and a fourth opening O4 arranged on opposite sides of the outer tube 2402 and corresponding to the first opening O1 and the second opening O2, respectively. As shown in FIG. 4(a), when the outer tube 2402 is rotated such that the third opening O3 is aligned with the first opening O1, the third opening O3 serve as the mist-exit port. Whereas, once the outer tube 2402 is rotated such that the fourth opening O4 is aligned with the second opening O2, the fourth opening O4 serve as the mist-exit port. The nutrient mists discharged from the mist-exit port will spray over the explants on the culture medium 27. In such configuration, the level of the mist-exit port above the culture medium 27 is adjustable according to the height or type of the explants. In such configuration, the level of the mist-exit port above the culture medium 27 is adjustable according to the height or type of the explants.

Referring again to FIG. 2, the light source 28 such as a LED lamp is provided beside the growth chamber 20 for metabolism of the explants. Alternatively, the light source 28 may be mounted within the growth chamber 20.

By the way, the rear side of the growth chamber 20 has two circular side doors 2031. The side doors 2031 are selectively opened for placing/removing the culture media 27 thereinto/therefrom. For example, the side doors 2031 can be opened in order to remove the culture media 27, which are then heat-sterilized in an autoclave. Moreover, the growth chamber 20 comprises a drain port 2021 at the bottom cover 202 for draining excess nutrient solution, and at least a vent 2011 at the top cover 201 for exhausting the un-reacted gas source and metabolic gases.

Figure 5:
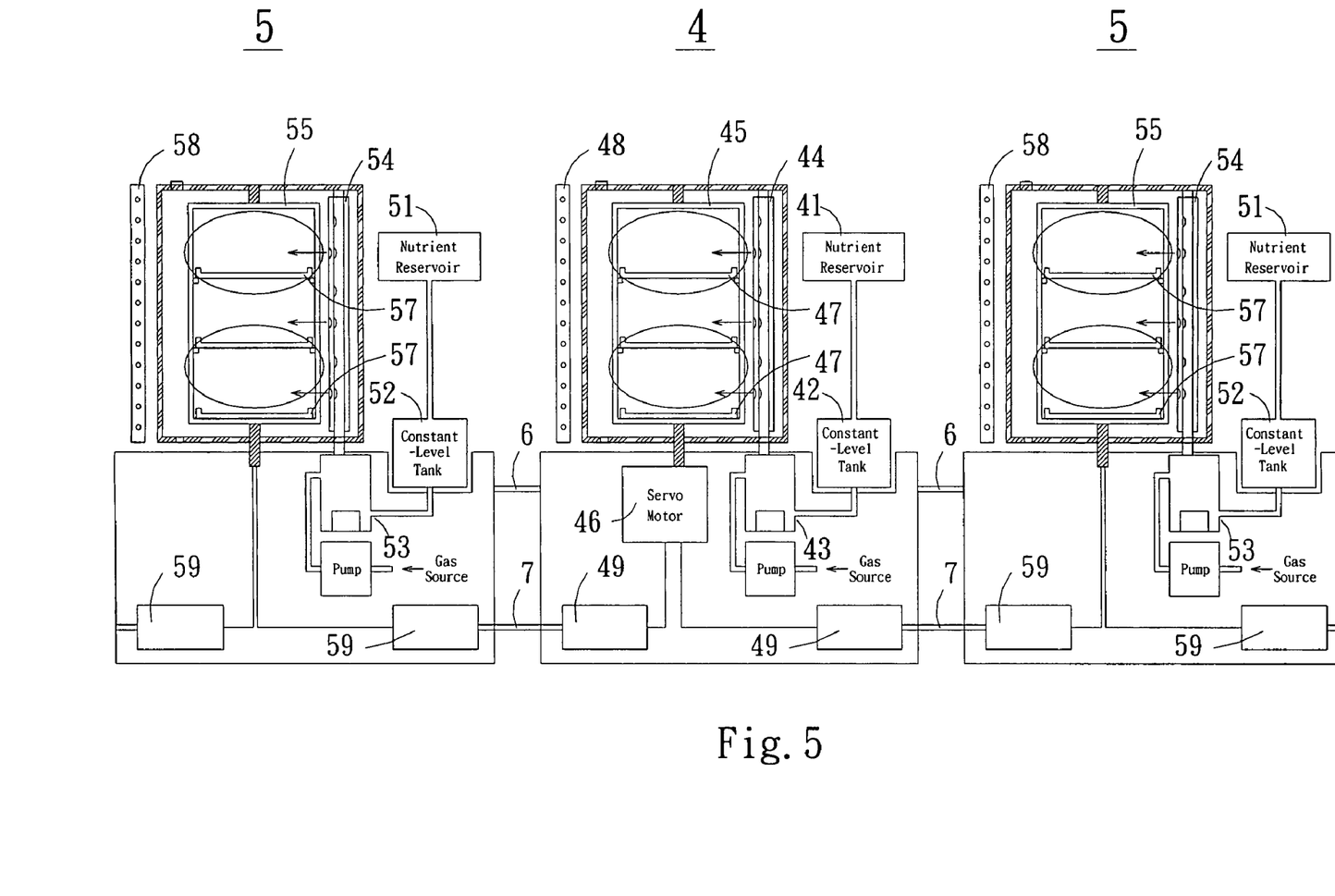
FIG. 5 schematically illustrates the combination of a main mist bioreactor with plural auxiliary mist bioreactors according to the present invention.

Please refer to FIG. 5, which is a schematic view showing the combination of a main mist bioreactor with plural auxiliary mist bioreactors according to the present invention. As shown in FIG. 5, the main mist bioreactor 4 comprises a nutrient reservoir 41, a constant-level tank 42, an ultrasonic mist generator 43, a mist delivery pipe 44, a rotatable culture bed 45, a servo motor 46, at least one culture medium 47, a light source 48 and one or more driving mechanism 49. Each auxiliary mist bioreactor 5 comprises a nutrient reservoir 51, a constant-level tank 52, an ultrasonic mist generator 53, a mist delivery pipe 54, a rotatable culture bed 55, at least one culture medium 57, optionally a light source 58 and one or more driving mechanism 59. A fastening device 6 can be employed to fasten the main mist bioreactor 4 with the auxiliary mist bioreactor 5. A transmission mechanism 7 can be employed to cooperate with the driving mechanism 59 of the auxiliary mist bioreactor 5 and the driving mechanism 49 of the main mist bioreactor 4 so that the rotatable culture bed 55 of the auxiliary mist bioreactor 5 can be rotated by the driving force derived from the servo motor 46 of the main mist bioreactor 4.

Figure 6:
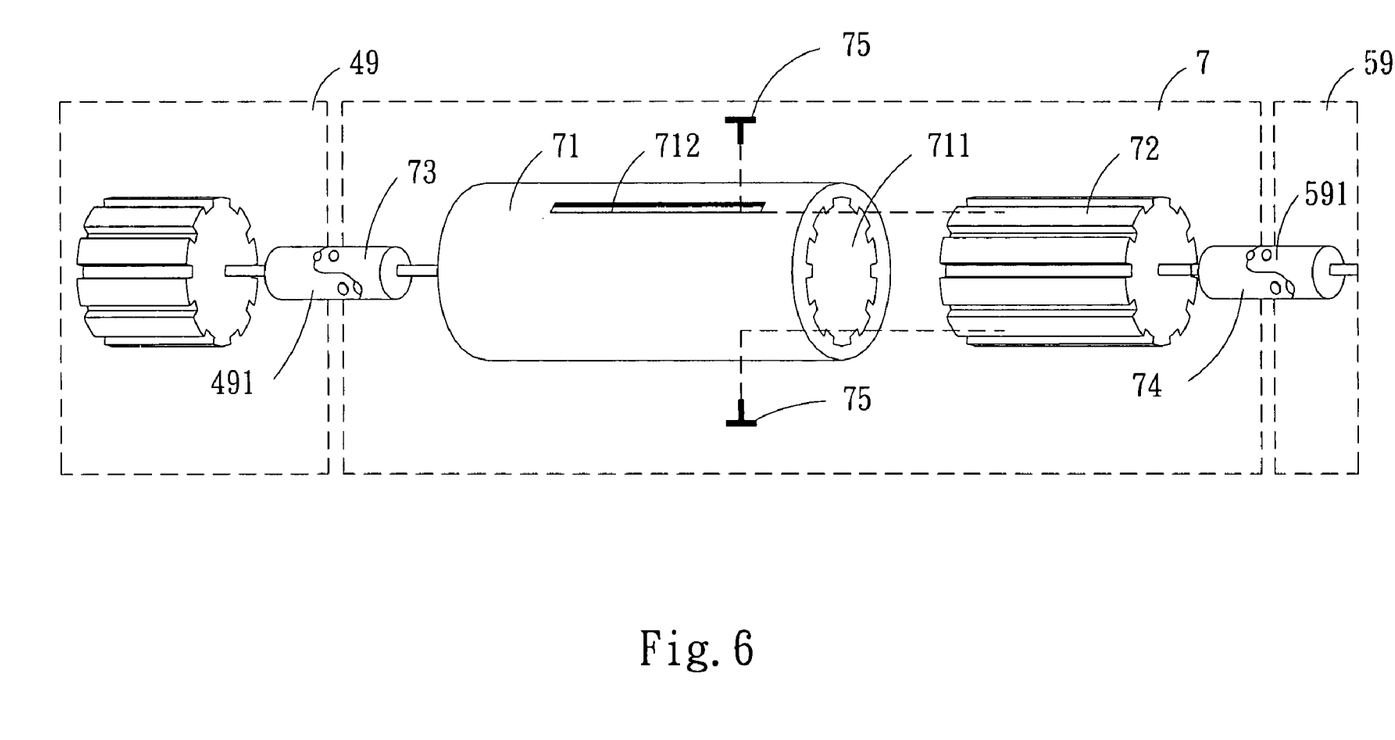
FIG. 6 schematically illustrates the transmission mechanism according to one preferred embodiment of the present invention.

Please refer to FIG. 6, which shows the transmission mechanism according to one preferred embodiment of the present invention. As shown in FIG. 6, the transmission mechanism 7 comprises a first transmission shift 71, a second transmission shift 72 and two connectors 73, 74. The first transmission shift 71 is hollow and has an inner wall 711 at sawtooth-shape, rectangle-shape or hexagon-shape. The first transmission shift 71 has a pair of slits 712 formed on the wall opposite to each other. The second transmission shift 72 has an outer wall at sawtooth-shape, rectangle-shape or hexagon-shape, which is the same with the inner wall of the first transmission shift 71. The second transmission shift 72 has a diameter substantially the same as that of the hollow portion of the first transmission shift 71 so that the second transmission shift 72 can rotate together with the first transmission shift 71. Two connectors 73, 74 are disposed on the end of the first transmission shift 71 and the end of the second first transmission shift 72, respectively. Two connectors 73, 74 are coupled to the connector 491 of the driving mechanism 49 of the main mist bioreactor 4 and the connector 591 of the driving mechanism 59 of the auxiliary mist bioreactor 5, respectively. Two screws 75 pass the slits 712 of the first transmission shift 72 and are secured to the second transmission shift 72 so that the second transmission shift 72 can slide within the hollow portion of the first transmission shift 71, thereby the length of the transmission mechanism 7 can be adjusted. Please refer to FIGS. 5 and 6 again. When the servo motor 46 of the main mist bioreactor 4 is activated, the driving mechanism 49 will be driven by the servo motor 46. Then, the driving mechanism 49 of the main mist bioreactor 4 will drive the transmission mechanism 7 to rotate so that the drive mechanism 59 of the auxiliary mist bioreactor 5 will be driven to rotate the rotatable culture bed 55.

From the above description, the nutrient mists can be uniformly distributed on the explants or plantlet in a short time period when the bioreactor of the present invention is used. In addition, the explants or plantlet are grown on non-pollutant conditions without additional processing operations such as pH adjustment or stirring operation. It is noted that, however, those skilled in the art will readily observe that numerous modifications and alterations of the connection member may be made while retaining the teachings of the invention. For example, the number of the culture media is advantageously increased and the related components of the bioreactor can be scaled up, thereby increasing the product yields. Accordingly, the above disclosure should be limited only by the bounds of the following claims.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A bioreactor for growing fungus, plant cell, tissue, organ, hairy roots and plantlet, comprising:
   a nutrient reservoir storing therein a nutrient solution required for said fungus, plant cell, tissue, organ, hairy roots and plantlet;
   a rotatable culture bed rotated at a specified speed and having a plurality of ring structures, wherein at least one of said ring structures has a plurality of protrusion structures;
   at least one culture medium having thereon said fungus, plant cell, tissue, organ, hairy roots and plantlet and supported on said rotatable culture bed by said protrusion structures;
   a mist generator for producing mists of said nutrient solution; and
   a mist delivery pipe delivering therein said mists of said nutrient solution and having a mist-exit port adjusted to a desired level above said culture medium so as to discharge and spray said mists over said fungus, plant cell, tissue, organ, hairy roots and plantlet.

2. The bioreactor according to claim 1 further comprising a constant-level tank disposed between said nutrient reservoir and said mist generator for ensuring that said nutrient solution flowing into said mist generator at a constant rate.

3. The bioreactor according to claim 2 wherein said mist generator is an ultrasonic mist generator, and comprises:
   a nutrient inlet for introducing said nutrient solution therethrough;
   an ultrasonic transducer for creating microwaves to energize said nutrient solution to create said mists; and
   a gas inlet for introducing a proper amount of gas sources necessary for cultivating said fungus, plant cell, tissue, organ, hairy roots and plantlet therethrough.

4. The bioreactor according to claim 3 further comprising a gas pump in upstream of said gas inlet for increasing the velocity of said gas sources flowing through said nutrient inlet.

5. The bioreactor according to claim 1 further comprising a servo motor for driving rotation of said rotatable culture bed.

6. The bioreactor according to claim 1 wherein said mist delivery pipe has a lower end in communication with said mist generator and a closed upper end.

7. The bioreactor according to claim 1 wherein said mist delivery pipe is arranged in an upright position.

8. The bioreactor according to claim 1 wherein said mist delivery pipe comprises:
   a fixed inner tube delivering therein said mists of said nutrient solution, and comprising first and second openings arranged on a side facing said rotatable culture bed; and
   a rotatable outer tube surrounding said inner tube, and comprising third and fourth openings corresponding to said first and second openings and arranged on opposite sides of said outer tube, respectively, wherein said third opening serves as said mist-exit port when said outer tube is rotated such that said third opening is aligned with said first opening, and said fourth opening serves as said mist-exit port when said outer tube is rotated such that said fourth opening is aligned with said second opening.

9. The bioreactor according to claim 1 further comprising a light source required for metabolism of said fungus, plant cell, tissue, organ, hairy roots and plantlet.

10. The bioreactor according to claim 9 wherein said light source is a LED lamp.

11. The bioreactor according to claim 1 wherein said rotatable culture bed, said culture medium and said mist delivery pipe are disposed within a growth chamber.

12. The bioreactor according to claim 11 wherein said growth chamber further comprises a drain port at the bottom thereof for draining excess nutrient solution.

13. The bioreactor according to claim 11 wherein said growth chamber further comprises at least a vent at the top thereof.

14. The bioreactor according to claim 11 wherein said growth chamber further comprises at least a side door selectively opened for placing said culture medium thereinto or removing said culture medium therefrom.

15. The bioreactor according to claim 1 wherein said plurality of ring structures of said rotatable culture bed comprise a lower end ring, a top end ring, and at least one intermediate ring.

16. The bioreactor according to claim 15 wherein said lower end ring, said top end ring and said at least one intermediate ring are jointed together by more than two upright posts.

17. The bioreactor according to claim 15 wherein said top and lower end rings have several first ribs extended to center portions thereof.

18. A bioreactor assembly for growing fungus, plant cell, tissue, organ, hairy roots and plantlet, comprising:
   a main bioreactor comprising
      a nutrient reservoir storing therein a nutrient solution required for said fungus, plant cell, tissue, organ, hairy roots and plantlet;
      a rotatable culture bed rotated at a specified speed and having a plurality of ring structures, wherein at least one of said ring structures has a plurality of protrusion structures;
      at least one culture medium having thereon said fungus, plant cell, tissue, organ, hairy roots and plantlet and supported on said rotatable culture bed by said protrusion structures;
      a mist generator for producing mists of said nutrient solution;
      a mist delivery pipe delivering therein said mists of said nutrient solution and having a mist-exit port adjusted to a desired level above said culture medium so as to discharge and spray said mists over said fungus, plant cell, tissue, organ, hairy roots and plantlet;
      a servo motor for driving rotation of said rotatable culture bed; and
      at least one driving mechanism coupled to the servo motor and driven by the servo motor;
   at least one auxiliary bioreactor comprising
      a nutrient reservoir storing therein a nutrient solution required for said fungus, plant cell, tissue, organ, hairy roots and plantlet;
      a rotatable culture bed rotated at a specified speed and having a plurality of ring structures, wherein at least one of said ring structures has a plurality of protrusion structures;
      at least one culture medium having thereon said fungus, plant cell, tissue, organ, hairy roots and plantlet and supported on said rotatable culture bed by said protrusion structures;
      a mist generator for producing mists of said nutrient solution;
      a mist delivery pipe delivering therein said mists of said nutrient solution and having a mist-exit port adjusted to a desired level above said culture medium so as to discharge and spray said mists over said fungus, plant cell, tissue, organ, hairy roots and plantlet; and
      at least one driving mechanism coupled to said rotatable culture bed;
   a transmission mechanism coupled to said driving mechanism of said main bioreactor and said driving mechanism of said auxiliary bioreactor for allowing said rotatable culture bed of said auxiliary bioreactor to rotate by the servo motor of the main bioreactor.

19. A bioreactor assembly according to claim 18 further comprising a fastening device disposed between said main bioreactor and said auxiliary bioreactor for fastening said main bioreactor and said auxiliary bioreactor.

* * * * *